US009795533B2

(12) United States Patent
Hatley

(10) Patent No.: US 9,795,533 B2
(45) Date of Patent: Oct. 24, 2017

(54) HOT TUB MANIFOLD WITH RAISED FRICTIONAL SECTIONS

(71) Applicant: LPI, Inc., Johnson City, TN (US)

(72) Inventor: David E. Hatley, Gray, TN (US)

( * ) Notice: Subject to any disclaimer, the term of this patent is extended or adjusted under 35 U.S.C. 154(b) by 67 days.

(21) Appl. No.: 14/820,093

(22) Filed: Aug. 6, 2015

(65) Prior Publication Data

US 2017/0035651 A1   Feb. 9, 2017

(51) Int. Cl.
  *E04H 4/00*   (2006.01)
  *A61H 33/00*  (2006.01)
  *A61N 5/06*   (2006.01)

(52) U.S. Cl.
  CPC ....... *A61H 33/601* (2013.01); *A61H 33/0087* (2013.01); *A61N 5/0616* (2013.01); *A61N 5/0618* (2013.01); *A61H 2033/0083* (2013.01); *A61H 2201/01* (2013.01); *A61H 2201/10* (2013.01); *A61N 2005/0663* (2013.01); *A61N 2005/0668* (2013.01)

(58) Field of Classification Search
  CPC .................................................. A61H 33/601
  USPC ...................................... 4/507, 541, 1, 541.6
  See application file for complete search history.

(56) References Cited

U.S. PATENT DOCUMENTS

| | | | |
|---|---|---|---|
| 2012/0174312 A1* | 7/2012 | Loyd ..................... | B05B 1/3026 4/541.6 |
| 2012/0192347 A1* | 8/2012 | Campbell ............ | A61H 33/601 4/541.6 |
| 2014/0101840 A1* | 4/2014 | Harder ............... | A61H 33/6052 4/541.6 |

* cited by examiner

*Primary Examiner* — Huyen Le
(74) *Attorney, Agent, or Firm* — Pitts & Lake, P.C.

(57) ABSTRACT

A hot tub manifold that has been engineered with a plurality of "teeth-like" raised sections inside the inner diameter of the manifold. As the water travels through the manifold while the hot tub pumps are operating, it travels across the surface of the "raised" sections creating friction. That friction energy created is thus transferred to the water in the form of heat—which in turn raises the temperature of the water to the desired set level on the thermostat on the hot tub. Passing the water (generally at high speed) over the raised teeth creates "free" heat and lowers the amount of time and energy required by the hot tub's element heater to elevate the water to the given temperature.

7 Claims, 2 Drawing Sheets

HOT TUB MANIFOLD WITH RAISED FRICTIONAL SECTIONS

CROSS-REFERENCE TO RELATED APPLICATIONS

This Application is a continuation-in-part of U.S. Provisional patent application Ser. No. 14/266,312, filed Apr. 30, 2014, which is incorporated herein by reference in its entirety and which claims priority to and claims the benefit of U.S. Provisional patent application Ser. No. 61/817,641, filed Apr. 30, 2013, the entirety of which is incorporated herein by reference.

STATEMENT REGARDING FEDERALLY SPONSORED RESEARCH OR DEVELOPMENT

Not Applicable

BACKGROUND OF THE INVENTION

1. Field of Invention

The present invention relates to hot tubs and to manifolds for hot tubs.

2. Description of the Related Art

Hot tubs and similar devices are used for recreation, exercise, and physical therapy. Hot tubs are often employed for treating sore muscles or for relaxation after exercise or rigorous physical activity.

SUMMARY OF THE INVENTION

The present invention includes, in some of its many embodiments, a molded PVC manifold for installation into the plumbing water line in a hot tub. The manifold according to the present general inventive concept is glued into place just like the standard manifolds used to plumb the hot tub. The "friction manifold" (or simply "manifold") is engineered with multiple (generally nine) "teeth-like" raised sections inside the inner diameter of the manifold. As the water travels through the manifold while the hot tub pumps are operating, it travels across the surface of the "raised" sections creating friction. That friction energy created is thus transferred to the water in the form of heat, which in turn raises the temperature of the water to the desired set level on the thermostat on the hot tub.

The present general inventive concept thus provides for a more energy-efficient and cost-efficient hot tub that is able to harness frictionally produced heat to achieve the desired environmental conditions within the hot tub. A hot tub according to the present general inventive concept thereby creates "free" heat and lowers the time in which the hot tubs element heater needs to operate in order to elevate the water to a set temperature.

In some example embodiments of the present general inventive concept, a friction manifold for a hot tub with a basin encompasses a portal through which water passes to enter the hot tub basin, said portal including a number of raised sections spaced around the interior perimeter of said portal, said raised sections to interact with water passing through said portal, whereby as water travels through the said portal, the water travels across the surface of the raised sections and creates frictional energy that is transferred to the water in the form of heat, thereby raising the temperature of the water.

In some embodiments, said portal includes nine raised sections.

In some embodiments, said friction manifold is fabricated from polyvinyl chloride (PVC).

BRIEF DESCRIPTION OF THE SEVERAL VIEWS OF THE DRAWING FIGURES

The above features, and other features and aspects of various example embodiments of the present general inventive concept, will become more apparent from examination of the drawing figures, in which.

DETAILED DESCRIPTION

The present invention includes, in some embodiments, a hot tub manifold that has been engineered with a plurality of "teeth-like" raised sections inside the inner diameter of the manifold. As the water travels through the manifold while the hot tub pumps are operating, it travels across the surface of the "raised" sections creating friction. That friction energy created is thus transferred to the water in the form of heat—which in turn raises the temperature of the water to the desired set level on the thermostat on the hot tub, thus creating "free" heat and lowering the time in which the hot tubs element heater needs to operate to elevate the water to the set temperature. The present general inventive concept thereby saves on costs for heating the hot tub.

Figure 1:
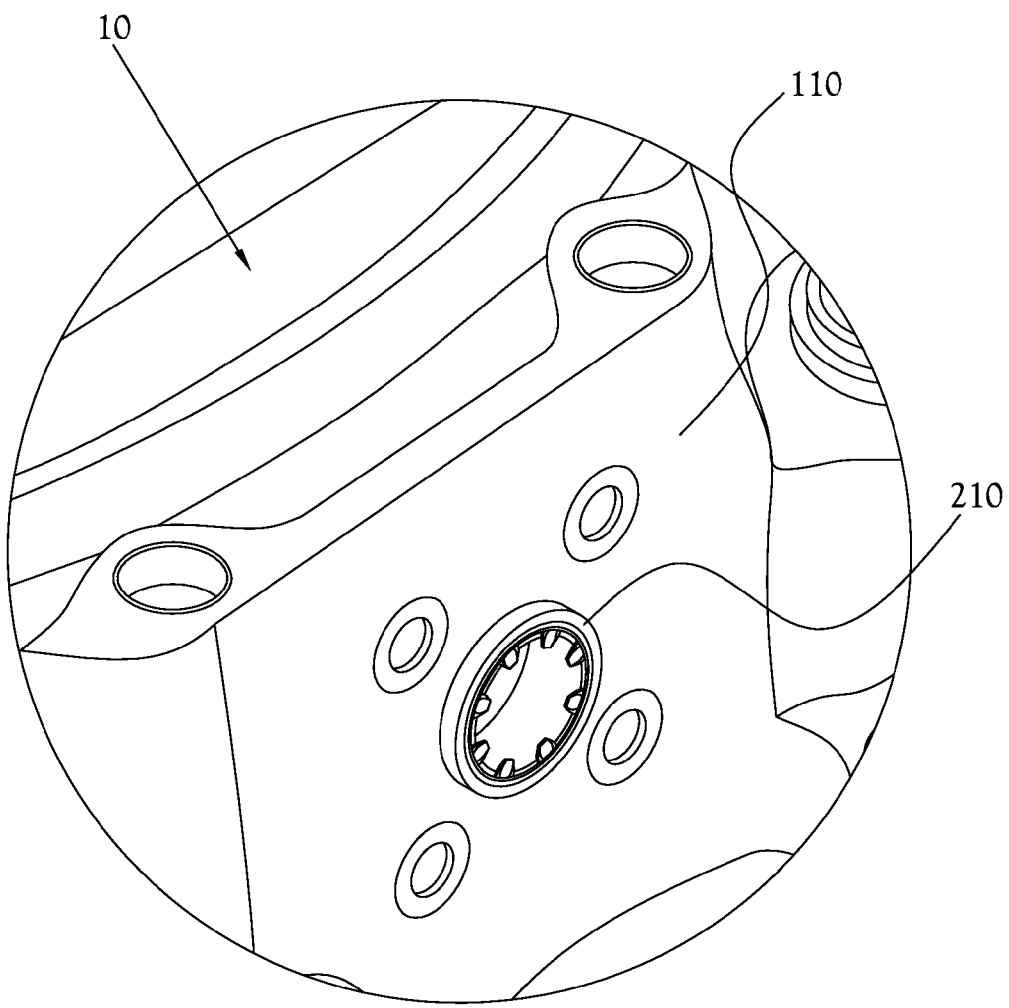
FIG. 1 shows a close-up view of an interior side wall of a hot tub, showing an example embodiment of a friction manifold in place on the port where plumbing line of the hot tub feeds water into the hot tub.
Figure 2:
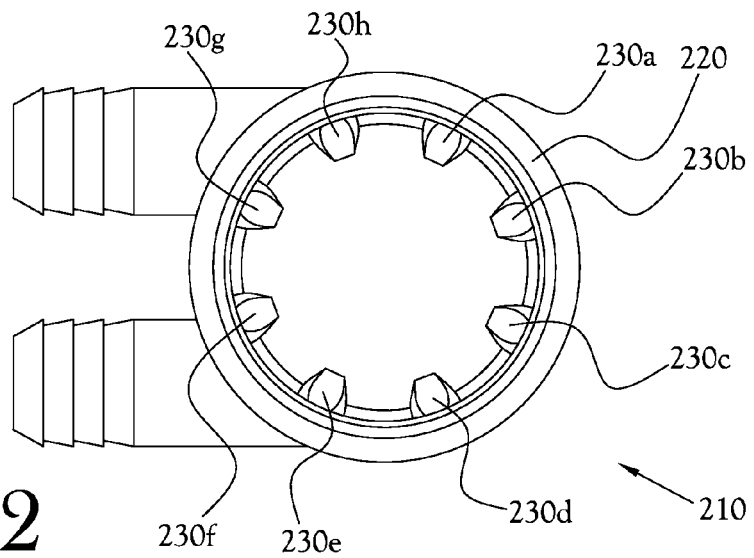
FIG. 2 is a view of one example embodiment of a friction manifold, showing the "raised teeth" within the mouth portal.
Figure 3:
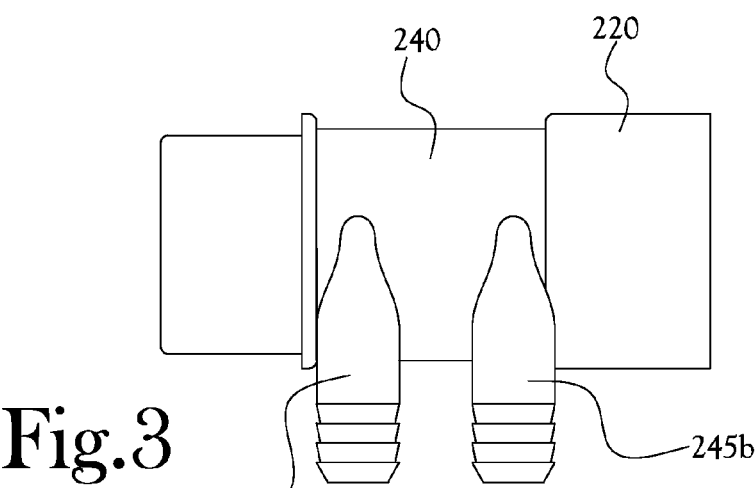
FIG. 3 is another view of the friction manifold shown in FIG. 2, showing two of the barbed ports.
Figure 4:
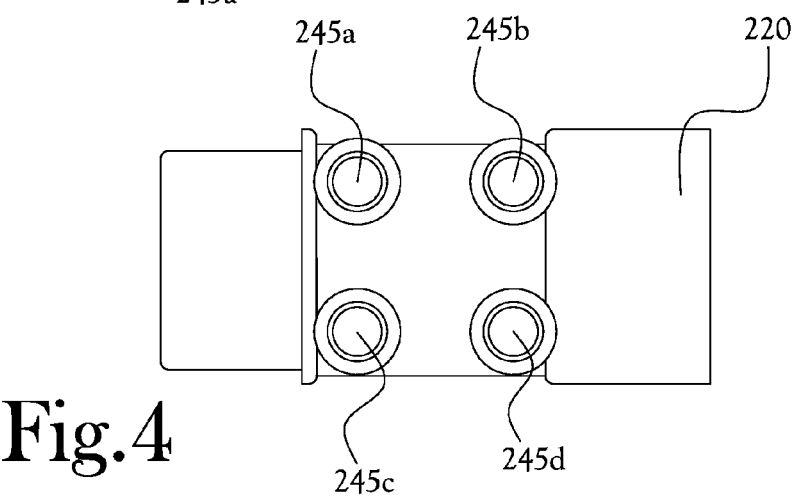
FIG. 4 is another view of the friction manifold shown in FIGS. 2 and 3, looking head-on at the four barbed ports of the illustrated example embodiment.

Turning to the Figures, FIG. 1 is a close-up view of an interior side wall 110 of a hot tub 10, showing the friction manifold 210 in place on the port where plumbing line of the hot tub 10 feeds water into the hot tub 10. FIGS. 2-4 present different views of the friction manifold 210, separated from the hot tub, showing generally the raised sections or "raised teeth" 230*a-h* that line the inner perimeter of the port mouth 220. Also shown, and best seen in FIGS. 3 and 4, are the barbed ports 245*a-d*, which each connect to water lines that supply water to the manifold 210. In operation, water passes through the barbed ports 245*a-d* into the interior of the manifold housing 240, and from there through the port mouth 220 into the basin of the hot tub 10; as the water passes through the port mouth 220, the water travels across the raised teeth 230*a-h*. The travel of the water across the raised teeth creates friction, which is transferred to the water in the form of heat, thereby raising the temperature of the water. Passing the water (generally at high speed) over the raised teeth creates "free" heat and lowers the amount of time and energy required by the hot tub's element heater to elevate the water to the given temperature. The present general inventive concept thereby saves on costs for heating the hot tub.

In some example embodiments of the present general inventive concept, a friction manifold for a hot tub with a basin encompasses a portal through which water passes to enter the hot tub basin, said portal including a number of raised sections spaced around the interior perimeter of said portal, said raised sections to interact with water passing through said portal, whereby as water travels through the said portal, the water travels across the surface of the raised sections and creates frictional energy that is transferred to the water in the form of heat, thereby raising the temperature of the water.

In some embodiments, said portal includes nine raised sections.

In some embodiments, said friction manifold is fabricated from polyvinyl chloride (PVC).

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A friction manifold for a hot tub with a basin, comprising:
    a portal through which water passes to enter the hot tub basin, said portal including a number of raised sections spaced around the interior perimeter of said portal, said raised sections configured to interact with water passing through said portal such that, as water travels through said portal, the water travels across the surface of the raised sections and creates frictional energy that is transferred to the water in the form of heat, thereby raising the temperature of the water; and
    wherein the raised sections are configured in a teeth-like form extending radially from the interior perimeter of the portal, the raised sections having a length and width greater than a thickness thereof, the thickness being in an axial direction of the portal.

2. The friction manifold of claim 1 wherein said portal includes nine raised sections.

3. The friction manifold of claim 1 wherein said friction manifold is fabricated from polyvinyl chloride.

4. The friction manifold of claim 1 wherein the raised sections are each configured to have a substantially flat surface, formed by the length and width, that is transverse to a direction of flow of the water passing through the portal.

5. A friction manifold to be used in a hot tub, comprising:
    a tubular inner surface; and
    a plurality of projections extending radially from the inner surface and configured to interact with water passing through the friction manifold;
    wherein the projections are configured in a teeth-like form having a length and width greater than a thickness thereof.

6. The friction manifold of claim 5, wherein the projections are each configured to have a substantially flat surface, formed by the length and width, that is transverse to a direction of flow of the water passing through the friction manifold.

7. The friction manifold of claim 5, wherein at least a portion of the plurality of projections are formed in a common plane that is perpendicular to an axis of the friction manifold.

* * * * *